(12) United States Patent
Kato

(10) Patent No.: US 7,832,926 B2
(45) Date of Patent: Nov. 16, 2010

(54) X-RAY RADIOGRAPHING APPARATUS

(75) Inventor: Katsushi Kato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/534,767

(22) Filed: Aug. 3, 2009

(65) Prior Publication Data

US 2010/0034354 A1 Feb. 11, 2010

(30) Foreign Application Priority Data

Aug. 5, 2008 (JP) .............................. 2008-201431

(51) Int. Cl.
*H01J 31/50* (2006.01)

(52) U.S. Cl. ...................................... 378/189; 378/197
(58) Field of Classification Search ................ 378/167, 378/197, 193–198
See application file for complete search history.

(56) References Cited

U.S. PATENT DOCUMENTS 6,412,978 B1 * 7/2002 Watanabe et al. ........... 378/197

FOREIGN PATENT DOCUMENTS

| JP | 11009579 A | 1/1999 |
| JP | 3388139 B2 | 3/2003 |
| JP | 2005-211226 A | 8/2005 |

* cited by examiner

*Primary Examiner*—Hoon Song
(74) *Attorney, Agent, or Firm*—Canon U.S.A. Inc., I.P. Division

(57) ABSTRACT

A coupler is provided with a protrusion and a flange-shaped locking portion. A case of an image receptor houses an X-ray detector and an unlocking mechanism including a movable locking portion. The movable locking portion is made to protrude into a depression by the urging force of a locking assist spring. When the case is attached to the coupler, the movable locking portion locks the locking portion, thereby holding the case and the coupler together. The central axis of the cylindrical surface of the depression corresponds to substantially the center of the X-ray detection area of the X-ray detector.

8 Claims, 12 Drawing Sheets

# X-RAY RADIOGRAPHING APPARATUS

BACKGROUND OF THE INVENTION

1. Field of the Invention

The present invention relates to an X-ray radiographing apparatus that detects X-rays passing through a subject and thereby obtains image information of the subject.

2. Description of the Related Art

As disclosed in Japanese Patent Laid-Open No. 2005-211226 and Japanese Patent No. 03388139, an X-ray radiographing apparatus includes an X-ray generator that emits X-rays, and an image receptor that houses an X-ray detector that detects X-rays. The X-ray generator and the image receptor are disposed opposite each other with a subject therebetween. By detecting X-rays passing through the subject, image information is obtained.

With the recent development of digital technologies, X-ray detectors using various image pickup devices that convert X-ray information into an electrical signal are making a significant progress, and digital radiographing apparatuses are becoming popular. Digital radiographing apparatuses are beginning to be introduced into many facilities, as a substitute for analogue radiographing apparatuses using a conventional film-screen method using a fluorescent member and a photosensitive film.

A solid-state flat detector, which is a typical digital X-ray detector, includes pixels and X-ray detecting elements that are thin-film transistors (TFTs). The pixels and the X-ray detecting elements are arranged in a two-dimensional array. X-rays incident on a pixel are converted into visible light by a fluorescent member. An electrical charge according to the visible light is generated by a photodiode. This electrical charge is temporarily stored in a capacitor. This stored electrical charge is read out pixel by pixel for each line, and is output as image information.

Since this image information is an electrical signal, digital radiographing apparatuses can handle not only a still image but also a moving image or a three-dimensional image information reconstructed by a computer from a plurality of projection images, and can be used to radiograph various areas of body and in various diagnosis fields.

FIG. 12 is a circuit configuration block diagram of such an X-ray radiographing apparatus. By operating an operating portion 1, a radiographing start command is output. Controlled by a control unit 2, an X-ray generator 3 emits an appropriate dose of X-rays. At the same time, the control unit 2 transmits a detection start command to an image receptor 4. The image receptor 4 detects X-rays emitted from the X-ray generator 3 and converts them into an electrical signal. This electrical signal is input into an image processor 5, undergoes appropriate image processing, and is then transferred to a display 6 and displayed as a visible image.

FIG. 13 schematically shows an X-ray radiographing apparatus for taking still images of the chest and abdomen of a subject M in the upright position. A support 11 is set upright in front of the subject M. An image receptor 4 is attached to the support 11 using a coupler 12 so as to be movable in the vertical direction. A case 13 of the image receptor 4 houses an X-ray detector 14.

Behind the subject M, an X-ray generator 3 that generates X-rays is attached to a telescopic support 15 hanging, for example, from the ceiling. The X-ray generator 3 is housed in a case 16. The case 16 houses an X-ray tube 17 and an X-ray restrictor 18. The X-ray tube 17 has a high voltage source (not shown). The height of the X-ray generator 3 can be adjusted to the subject M and the image receptor 4 by the telescopic mechanism of the support 15. Instead of hanging from the ceiling using the support 15, the case 16 can be supported by a support attached to the floor or the wall.

FIG. 14 schematically shows an X-ray radiographing apparatus for radiographing a subject M in the recumbent position on a bed. When radiographing such a subject M in the recumbent position, a moving image as well as still images of each part of the human body is often taken. A stereo image is constructed by processing a plurality of projection images. Various types of radiographing can be performed.

A support 21 supports a C-shaped arm 23 with a guide member 22 therebetween. At one end of the C-shaped arm 23 is the same image receptor 4 of FIG. 13, and at the other end is the same X-ray generator 3 of FIG. 13. The subject M is placed on a bed 25 disposed between the image receptor 4 and the X-ray generator 3 of the C-shaped arm 23.

In FIG. 14, the X-ray generator 3, the subject M, and the image receptor 4 are arranged in this order as in FIG. 13. The C-shaped arm 23 can be angled by a mechanism of the guide member 22. In an X-ray radiographing apparatus using a C-shaped arm 23, the positional relationship between the X-ray generator 3 and the image receptor 4 is fixed. Therefore, the process of adjusting the positional relationship is omissible. Therefore, this type of apparatus is convenient for radiographing in which the radiographing angle is frequently changed. However, the distance between the X-ray generator 3 and the image receptor 4 is difficult to change. Therefore, this type of apparatus is unfit for some types of radiographing.

The image receptor 4 can be used without being supported by any support. That is to say, the image receptor 4 can be used as a so-called electronic cassette. In this case, the image receptor 4 can be freely disposed above, for example, a bed, like a film cassette, and the degree of freedom of the positional relationship between the subject M and the image receptor 4 is increased.

As described above, according to the type of radiographing, the image receptor 4 is attached to an upright support or a C-shaped arm 23, or freely disposed as an electronic cassette. However, a radiographing apparatus including an X-ray detector using various types of image pickup devices and the maintenance cost thereof are expensive depending on the function and performance. Therefore, it is not economical for a facility to own many radiographing apparatuses corresponding to a wide variety of cases.

To solve this problem, an X-ray radiographing apparatus is widespread that has an X-ray detector that can be easily attached to and detached from a plurality of types of supports and therefore can be used in various types of radiographing. In addition, an X-ray radiographing apparatus is proposed that has an image receptor 4 that can detect X-rays without being supported by a support and can be used as an electronic cassette, like a film cassette, when detached from a support.

Further, although the purpose is different, a fitting locking mechanism is proposed that enables a case of an image receptor housing an X-ray detector to be attached to and detached from a coupler of a C-shaped arm. However, in the case of a support typified by a C-shaped arm that fixes the positional relationship between the X-ray generator 3 and the image receptor 4, the positional relationship between the X-ray irradiation axis and the X-ray detector needs to be sufficiently accurate. If the accuracy is insufficient, a favorable image may not be able to be obtained, and in addition, the surroundings of the area to be exposed may be needlessly exposed to X-rays.

The X-ray generator 3 is provided with an X-ray restrictor 18 for adjusting the area to be irradiated with X-rays. It is desirable that the shape and position of the X-ray restrictor 18 accurately correspond to the shape and position of the image reception area of the X-ray detector 14. In general, the image reception area of a solid-state flat detector is rectangular. In that case, the shape of the X-ray restrictor 18 needs to be a similar rectangle, and the position of the X-ray restrictor 18 in the direction of rotation around the X-ray irradiation axis is made to correspond to that of the image reception area of the X-ray detector 14. Therefore, when the image receptor 4 separated from a support is re-attached to the support, the image receptor 4 needs to be attached in the original position.

However, the X-ray detector 14 has a large projected area in a plane perpendicular to the X-ray irradiation axis, to ensure the necessary size for the detection area. In addition, to ensure the rigidity necessary to drive the X-ray detector 14 under favorable conditions, the case 13 of the image receptor 4 housing the X-ray detector 14 is liable to be heavy. The case 13 is difficult for the operator to lift. Sometimes the case 13 is difficult to attach in its correct position.

Even if a marker for position adjustment and fitting locking portions are provided, it takes time to find the marker for position adjustment depending on the position of the support and the position of the hand of the operator when lifting the case 13 of the image receptor 4.

SUMMARY OF THE INVENTION

The present invention provides such an X-ray radiographing apparatus that an image receptor can be attached to a coupler without regard to the position in the angular direction, the operation is therefore easy to understand, the attachment is completed in a short time despite a heavy and large case of the image receptor, and the burden on the operator can be reduced.

In an aspect of the present invention, an X-ray radiographing apparatus includes an X-ray detecting unit that detects X-rays passing through a subject, an image receptor housing the X-ray detecting unit, a support that supports the image receptor, and a coupler for detachably coupling the image receptor with the support. The coupler and the image receptor can be coupled with each other at any angle with respect to the direction of rotation around an axis perpendicular to the image reception surface.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

The embodiments of the present invention will now be described in detail with reference to FIGS. 1 to 11.

First Embodiment

Figure 1:
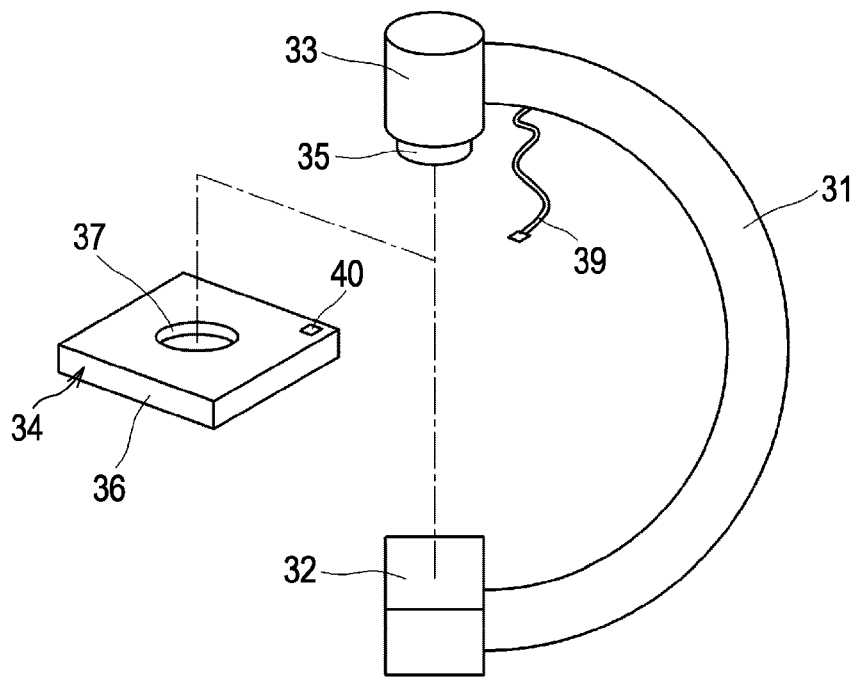
FIG. 1 is a schematic perspective view of an X-ray radiographing apparatus according to a first embodiment.

FIG. 1 is a schematic perspective view of an X-ray radiographing apparatus in this embodiment. At one end of a C-shaped arm 31 is an X-ray generator 32, and at the other end is a coupler 33. The coupler 33 is provided with a cylindrical protrusion 35 for attaching an image receptor 34. The central axis of the cylindrical surface of the protrusion 35 corresponds to the incident axis of X-ray irradiation from the X-ray generator 32.

The image receptor 34 is housed in a case 36. The case 36 has a depression 37 formed in the surface opposite the X-ray detection surface. The depression 37 is cylindrical and centered on an axis perpendicular to the detection surface and passing through substantially the center of the detection area. Thereunder is an X-ray detector 38 with the image reception surface down. The C-shaped arm 31 houses a cable 39 for making electrical connection with the image receptor 34. The image receptor 34 is provided with a socket 40 to which the cable 39 is connected.

Figure 2:
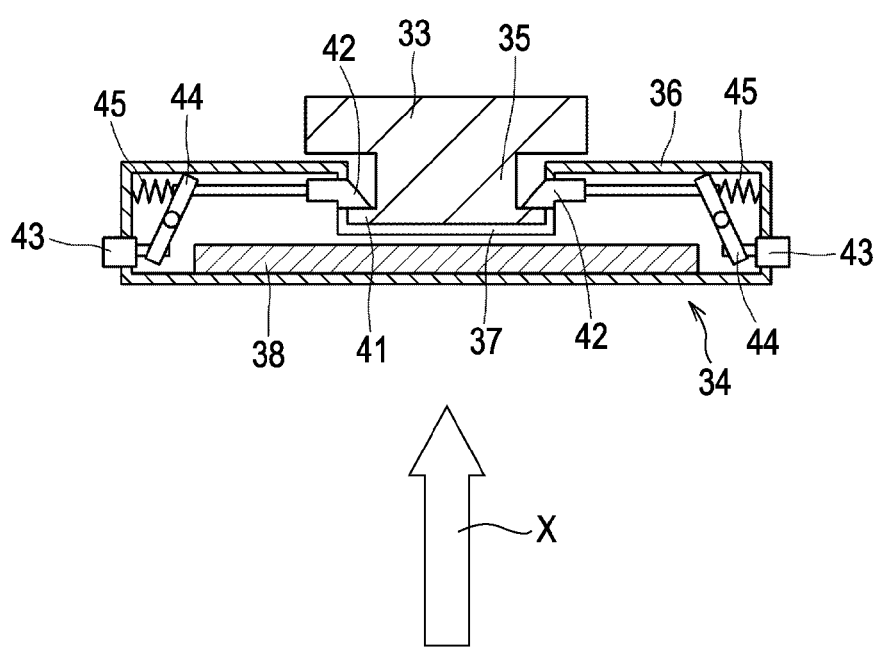
FIG. 2 is a sectional view of an image receptor and a coupler.

FIG. 2 is a sectional view of the coupler 33 and the case 36, with the protrusion 35 fitted in the depression 37, taken along a plane passing through the central axes of both cylindrical surfaces. The arrow X shows the X-ray irradiation direction.

The central axis of the cylindrical surface of the depression 37 corresponds to substantially the center of the X-ray detection area of the X-ray detector 38. The depression 37 has such a shape that the protrusion 35 of the coupler 33 can fit into the depression 37. When the protrusion 35 is fitted in the depression 37, the X-ray incident axis corresponds to the center of the X-ray detection area of the image receptor 34. Therefore, the need for centering after attaching is eliminated. After attaching the image receptor 34 to the coupler 33, the cable 39 is connected to the socket 40 of the case 36. This enables the C-shaped arm 31 and the image receptor 34 to electrically communicate with each other, the image receptor 34 to be supplied with power, and the X-ray detector 38 of the image receptor 34 to operate.

Instead of providing the C-shaped arm 31 with a cable 39 and the image receptor 34 with a socket 40, the C-shaped arm 31 may be provided with a socket 40 and the image receptor 34 may be provided with a cable 39. Alternatively, both the C-shaped arm 31 and the image receptor 34 may be provided with a cable 39, and the ends of the cables may be connected by an intermediate connector. Instead of providing a cable 39, a slip-ring electrical connection may be provided between the protrusion 35 of the coupler 33 and the depression 37 of the image receptor 34 for electrical communication. Alternatively, wireless communication may be used.

By providing a battery in the case 36, power can be supplied without using a cable 39. If the cable 39 has a sufficient length, the coupler 33 and the image receptor 34 may always be connected by the cable 39 without disconnecting the cable 39.

The coupler 33 is provided with a flange-shaped locking portion 41 as well as the protrusion 35. The case 36 houses unlocking mechanisms as well as the X-ray detector 38. The unlocking mechanisms each include a movable locking portion 42, an unlocking button 43, an unlocking link lever 44, and a locking assist spring 45. The movable locking portions 42 are made to protrude from the cylindrical surface of the depression 37 by the urging force of the locking assist springs 45. When the image receptor 34 is attached to the coupler 33, the locking portion 41 is locked by the movable locking portions 42 to hold the image receptor 34 and the coupler 33 together. In this embodiment, two opposed movable locking portions 42 are provided, and two unlocking mechanisms corresponding to the movable locking portions 42 are provided.

To detach the image receptor 34 from the coupler 33, the unlocking mechanisms are operated by pressing the unlocking buttons 43 provided in the outer frame of the case 36. Pressing the unlocking buttons 43 rotates the unlocking link levers 44 around their fulcrums, and the movable locking portions 42 are moved out of the depression 37. When the movable locking portions 42 are retracted, the latched state of the movable locking portions 42 and the locking portion 41 is eliminated. The operator separates the case 36 from the coupler 33, thereby detaching the image receptor 34 from the coupler 33.

As an alternative to the example of FIG. 2, two or more movable locking portions 42 may be operated at the same time by pressing a single unlocking button 43, using an interlocking mechanism housed in the case 36. In that case, the operator only has to press a single unlocking button 43, and therefore unlocking can be performed with simple operation.

When attaching the image receptor 34, the operator moves the case 36 toward the coupler 33 and fits the protrusion 35 into the depression 37 while pressing the unlocking buttons 43. When the protrusion 35 has been fully fitted in the depression 37, the operator releases the unlocking buttons 43. The movable locking portions 42 are made to protrude from the cylindrical surface of the depression 37 by the urging force of the locking assist springs 45 and lock the locking portion 41 to hold the image receptor 34 and the coupler 33 together. Alternatively, if the movable locking portions 42 is provided with a tapered surface, the movable locking portions 42 move in conjunction with the fitting of the protrusion 35 into the depression 37, the operator need not keep the unlocking buttons 43 pressed, and therefore the operation is made easier.

As described above, by providing unlocking buttons 43 in the outer frame of the case 36, the operator can perform the pressing of the unlocking buttons 43 and the supporting of the case 36 at the same time. In addition, by providing two diametrically opposed unlocking buttons 43, the operator can hold the case 36 more stably. The operator needs to operate the two unlocking buttons 43 at the same time to detach the image receptor 34 from the coupler 33. Therefore, the operator always holds the image receptor 34 with both hands and cannot holds the image receptor 34 with only one hand, unstably. Therefore, the operator is prevented from dropping the image receptor 34, breaking it, and damaging people or objects around.

Due to this configuration, position adjustment of the image receptor 34 and the coupler 33 is completed just by fitting the protrusion 35 into the depression 37. Since the image receptor 34 can be attached to the coupler 33 without regard to the position in the angular direction, the operation is easy to understand and simple, the attachment is completed in a short time despite the heavy and large case 36, and the burden on the operator can be reduced. When the attachment is completed, the position coordinate adjustment of the X-ray incident axis and the X-ray detection area is also completed. Therefore, further position adjustment can be omitted, and efficient preparation for radiographing can be performed.

Second Embodiment

Figure 3A:
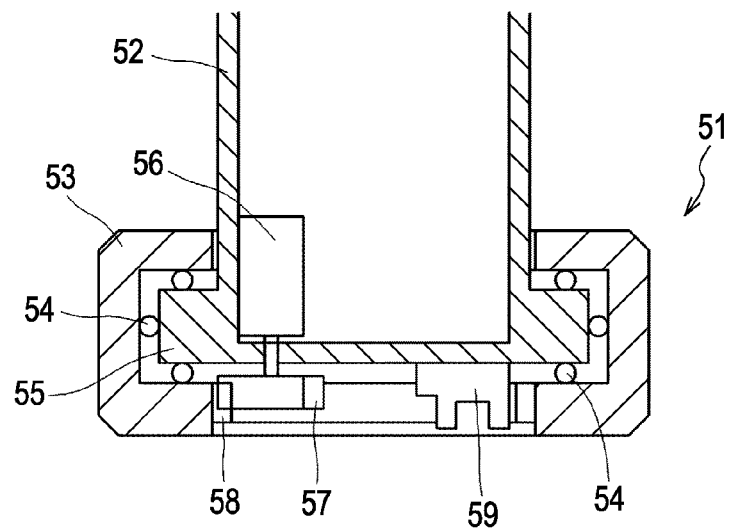
FIGS. 3A and 3B are sectional views of an image receptor and a coupler according to a second embodiment.
Figure 3B:
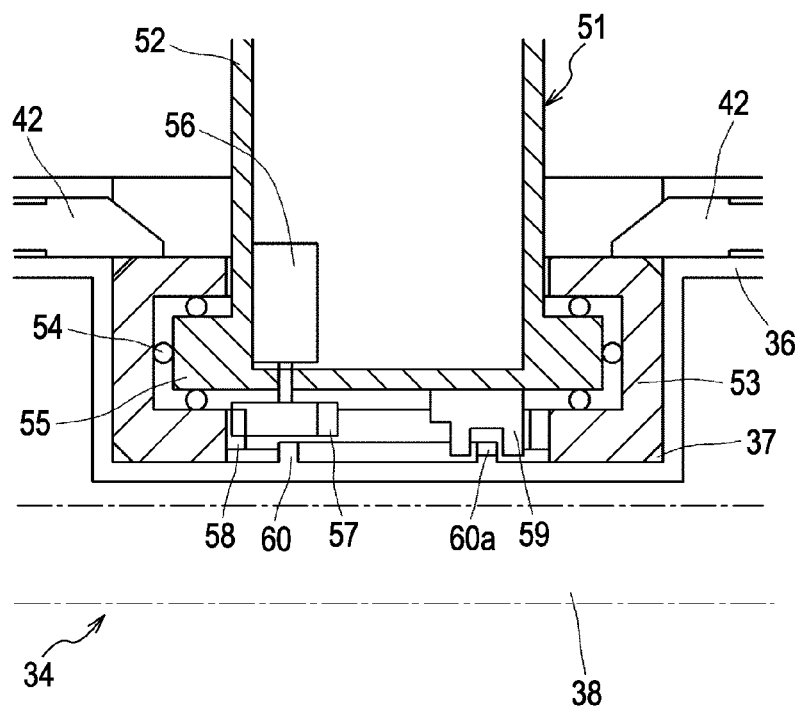

FIG. 3A is a sectional view of a coupler of a second embodiment, and FIG. 3B is a sectional view of the coupler with an image receptor attached thereto. In FIG. 3A, the coupler 51 includes a base shaft 52 and an outer ring 53, which are coaxial. Between the base shaft 52 and the outer ring 53 are a plurality of bearing balls 54 so that the outer ring 53 can smoothly rotate relative to the base shaft 52 around the axis. At the lower end of the base shaft 52 is formed a flange 55, which has many surfaces that receive the bearing balls 54. Therefore, the forces in all radial directions and the thrust direction can be received by the bearing balls 54. As a substitute for a mechanism using bearing balls 54, various types of bearings may be used, for example, cylindrical rollers, conical (tapered) rollers, a sliding bearing, or a fluid bearing.

Inside the base shaft 52 is provided a motor 56. The output shaft of the motor 56 is connected to an external gear 57 exposed outside the base shaft 52. On the other hand, the outer ring 53 is provided with an internal gear 58 coaxial with the outer ring 53. The internal gear 58 is meshed with the external gear 57. Due to this configuration, the outer ring 53 can be freely rotated by rotating the motor 56. The base shaft 52 is provided with a photointerrupter 59. The photointerrupter 59 outputs a signal of "OFF" when the light path is blocked, and outputs a signal of "ON" when the light path is not blocked. The roll of this photointerrupter 59 will hereinafter be described.

In FIG. 3B, the basic configuration of the surroundings of the depression 37 of the case 36 housing the image receptor 34 is the same as the configuration described in the first embodiment. The depression 37 is provided with the movable locking portions 42, which lock the coupler 51. However, in the second embodiment, the outer surface of the coupler 51 is that of the outer ring 53. When the movable locking portions 42 protrude, the outer ring 53 and the case 36 are held together. By rotating the motor 56, the case 36 is rotated together with the outer ring 53. To hold the outer ring 53 and the case 36 together with a high degree of accuracy, the friction between the case 36 and the outer ring 53 or between the movable locking portions 42 and the outer ring 53 may be increased. Alternatively, the cylindrical surfaces of the case 36 and the outer ring 53 may be provided with fine teeth to mesh with each other.

On the bottom surface of the depression 37 of the case 36 is formed a ring-shaped protrusion 60. This ring-shaped protrusion 60 is located at such a position and has such a height that the ring-shaped protrusion 60 blocks the light from the photointerrupter 59 when the case 36 is attached to the coupler 51. The ring-shaped protrusion 60 has a gap 60a, thus being C-shaped. The gap 60a allows the light from the photointerrupter 59 to pass through when the case 36 is attached to the coupler 51. While the case 36 makes a 360 degree rotation relative to the base shaft 52, the output signal of the photointerrupter 59 is "OFF" except for a short period of time when the output signal of the photointerrupter 59 is "ON" due to the gap 60a. By using the switching of the output signal, a unit that detects the initial position of a standard rotating body can be constructed in a simple structure and at low cost.

Figure 4:
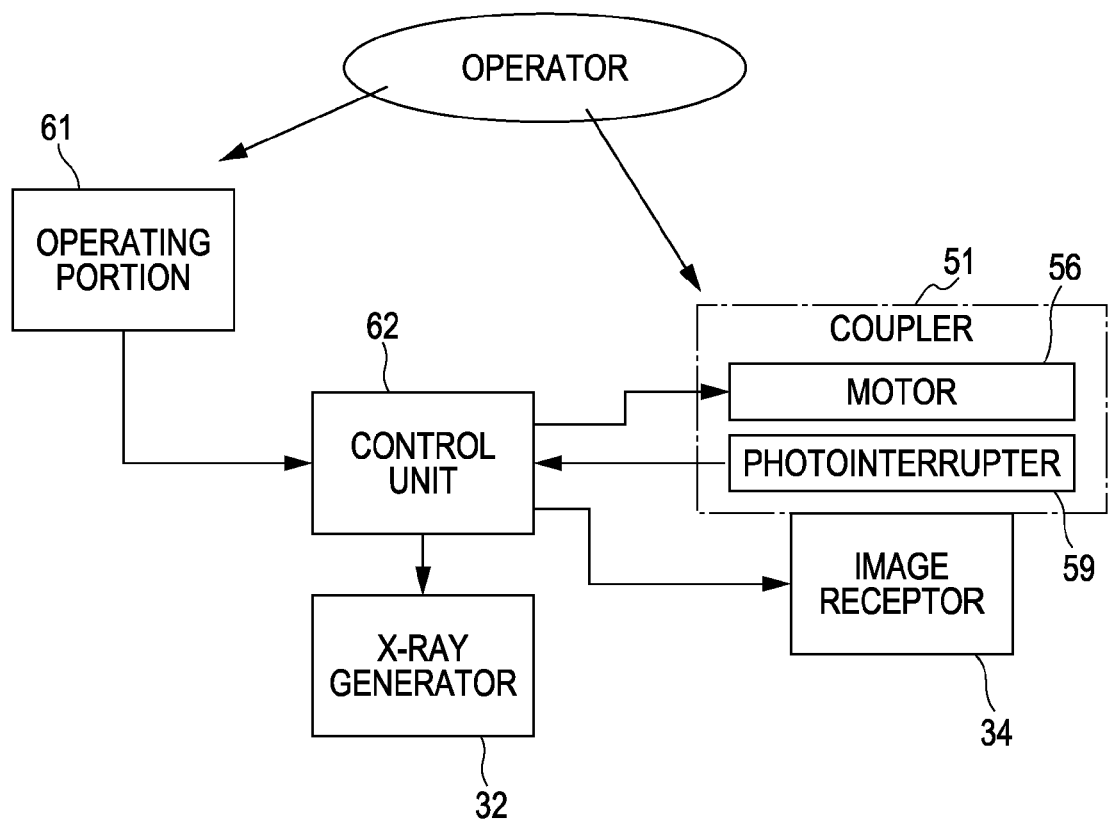
FIG. 4 is a circuit configuration block diagram of an X-ray radiographing apparatus.

FIG. 4 is a circuit configuration block diagram of an X-ray radiographing apparatus. The output of an operating portion 61 is connected to a control unit 62. The output of the control unit 62 is connected to an X-ray generator 32 and an image receptor 34. The output of the control unit 62 is also connected to a motor 56 of a coupler 51. The output of a photointerrupter 59 is connected to the control unit 62.

Figure 5:
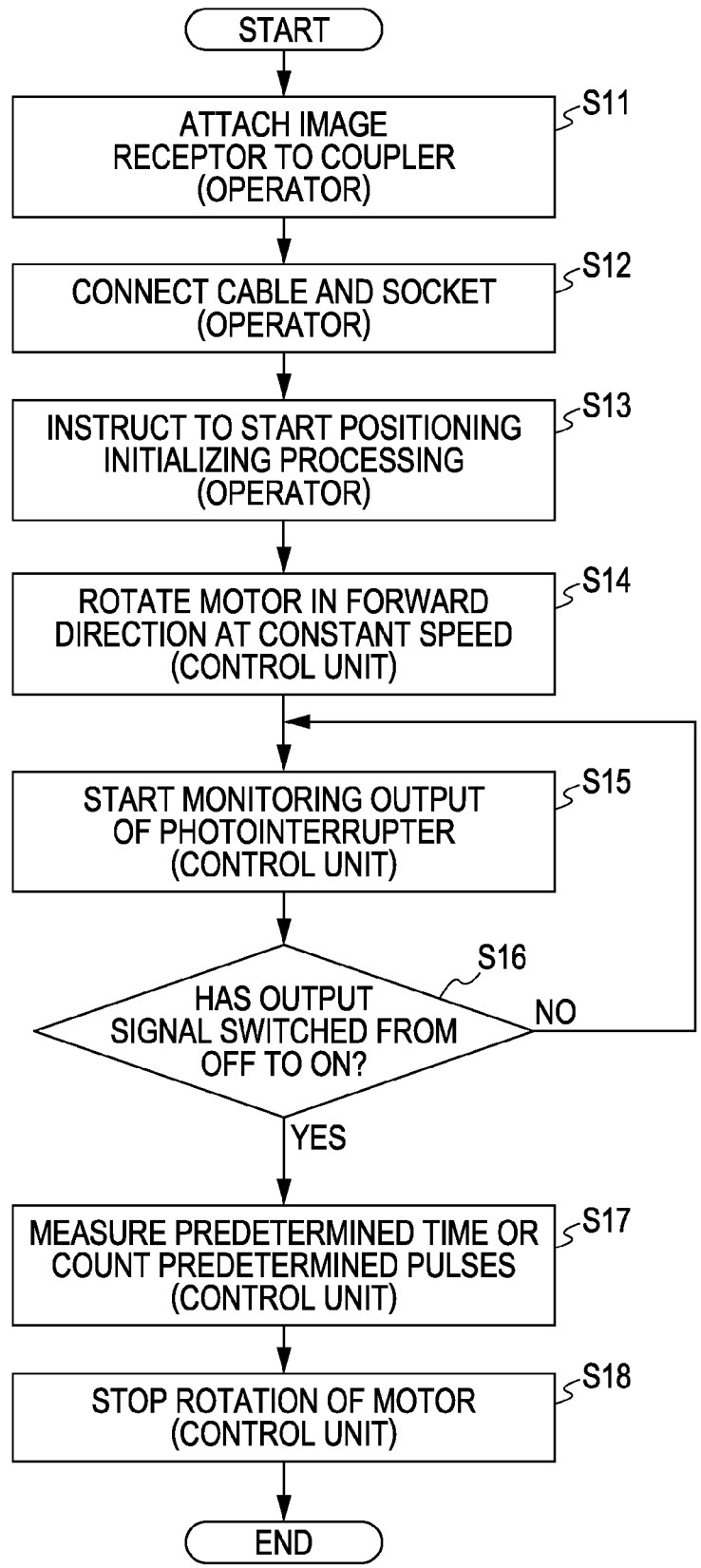
FIG. 5 is a flowchart showing initialization for positioning the image receptor.

FIG. 5 is a flowchart showing initialization for positioning the image receptor of the X-ray radiographing apparatus. The performer of each step is shown in parentheses.

Before the flow of FIG. 5, the image receptor 34 is separated from the coupler 51 of the C-shaped arm 31. When attaching the image receptor 34 to the C-shaped arm 31 to start radiographing, this flow is applied.

The operator attaches the image receptor 34 to the coupler 51 (step S11), connects the cable 39 and the socket 40 (step S12), and then instructs to start the positioning initializing processing from the operating portion 61. The control unit 62 transmits a signal and rotates the motor 56 in the forward direction at a constant speed (step S14). The forward direction is a predetermined direction. Whether clockwise or counterclockwise does not make any difference.

The control unit 62 starts monitoring the output signal of the photointerrupter 59 (step S15). Monitoring is continued until the output signal of the photointerrupter 59 has switched from OFF to ON (step S16). From the time the output signal has switched to ON, a predetermined time T is measured. In the case where the motor 56 is a pulse motor, instead of measuring a predetermined time T, a predetermined number of pulses P is counted (step S17). When the predetermined time T or number of pulses P is reached, the rotation of the motor 56 is stopped (step S18).

When attaching the image receptor 34 to the C-shaped arm 31 and starting radiographing, the position of the image receptor 34 relative to the C-shaped arm 31 in the direction of rotation around the X-ray irradiation axis can be reset to a predetermined initial position by performing this flow. To set the initial position, the predetermined time T or the predetermined number of pulses P is set to a desired appropriate value. If the value of the predetermined time T or the predetermined number of pulses P can be changed from the operating portion 61, the image receptor 34 can be set in a position convenient for the operator in each case.

Third Embodiment

Figure 6:
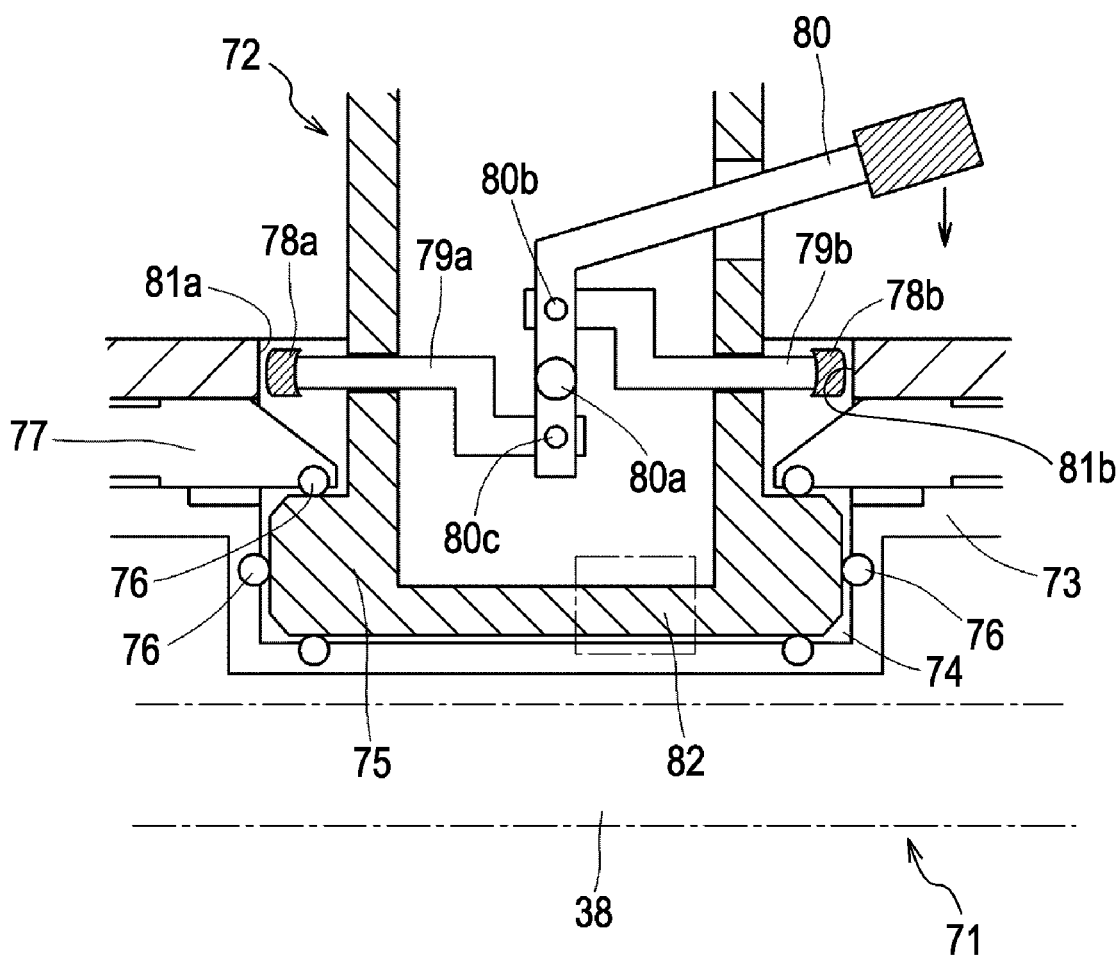
FIG. 6 is a sectional view of an image receptor and a coupler according to a third embodiment.

FIG. 6 is a sectional view of a third embodiment, which is suitable for an apparatus in which an X-ray generator and an image receptor are integrated by a C-shaped arm 31.

As in the first embodiment, in FIG. 6, an image receptor 71 is attached to a coupler 72. A case 73 housing the image receptor 71 is provided with a depression 74. Many bearing balls 76 for supporting a flange portion 75 of the coupler 72 are disposed in the depression 74. The movable locking portions 77 are also provided with bearing balls 76. By being supported by these bearing balls 76, the case 73 is held so as to be smoothly rotatable around the central axes of the flange portion 75 of the coupler 72 and the depression 74. Providing bearing units such as bearing balls enables the case 73 to be smoothly rotated just by applying a small force.

The coupler 72 is provided with a control unit for positionally fixing the image receptor 71. The control unit for positionally fixing the image receptor 71 includes brake shoes 78a and 78b, rods 79a and 79b, and an operating lever 80. When the operator holds the operating lever 80 and applies a force in the direction of the arrow, the operating lever 80 rotates around a fulcrum 80a and transmits force by leverage from points 80b and 80c of application of force to the rods 79a and 79b. The rods 79a and 79b move leftward and rightward, respectively, and press the brake shoes 78a and 78b, respectively, outward. The brake shoes 78a and 78b come into contact with the cylindrical wall surfaces 81a and 81b of the case 73.

The friction between the brake shoes 78a and 78b and the cylindrical wall surfaces 81a and 81b restricts the rotation of the image receptor 71 relative to the coupler 72. By fixing the operating lever 80 in this position, the rotation of the image receptor 71 relative to the coupler 72 can be kept restricted, and therefore the image receptor 71 can be prevented from being accidentally rotated. The position where the image receptor 71 is fixed can be selectively set.

Rotating the operating lever 80 in the reverse direction returns the image receptor 71 to the original rotatable state. Instead of manually restricting the rotation of the image receptor 71, the operating lever 80 may be moved by a motor or a hydraulic actuator controlled by a control unit.

In addition, a position detector 82 for detecting the position of the image receptor 71 relative to the coupler 72 in the direction of rotation is provided. This position detector 82 is such a position detector that can detect the displacement angle in the direction of rotation of the image receptor 71 relative to a reference position and transmit the displacement angle to the control unit 62 as electrical signal information. Therefore, common potentiometers and other various types of position detectors can be used, regardless of whether they are of contact type or contactless type.

Figure 7:
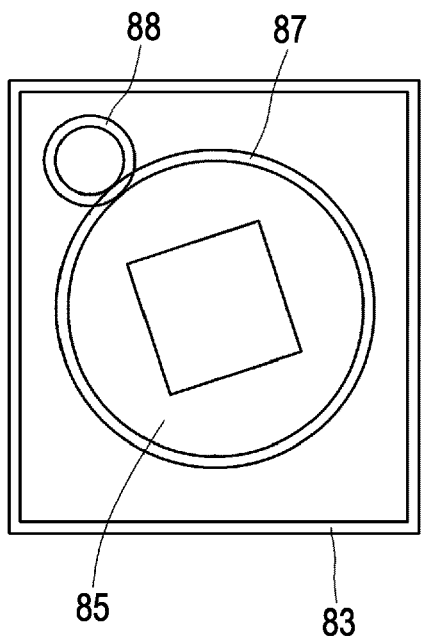
FIG. 7 is a sectional view of an X-ray generator.
Figure 8:
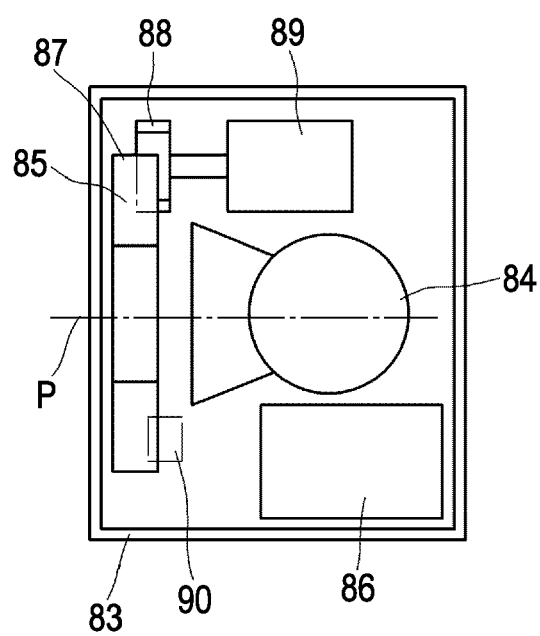
FIG. 8 is a configuration diagram of an X-ray restrictor.

FIG. 7 is a sectional view of the X-ray generator 32 taken along a plane passing through the X-ray irradiation axis of the X-ray generator 32. FIG. 8 is a configuration diagram of a X-ray restrictor as viewed from the X-ray irradiation side.

The case 83 of the X-ray generator 32 houses an X-ray tube 84, an X-ray restrictor 85, a high voltage source 86, and so forth. The X-ray restrictor 85 is a disk-shaped member having a rectangular opening in the center, and is formed of a material capable of blocking X-rays. The X-ray restrictor 85 blocks X-rays other than those passing through the central opening, thereby restricting the X-ray irradiation area.

In the third embodiment, the X-ray restrictor 85 is supported rotatably around an axis P. The axis P substantially corresponds to the X-ray irradiation axis of the X-ray tube 84, and passes through substantially the center of the X-ray detection area of the image receptor 71. The X-ray restrictor 85 has a gear 87 provided therearound. The gear 87 meshes with another gear 88. The gear 88 is attached to the output shaft of a motor 89.

By driving the motor 89, the gears 88 and 87 are rotated, and the X-ray restrictor 85 can be rotationally driven around the axis P. To detect the rotational position of the X-ray restrictor 85, a position detector 90 is provided, which has the same configuration as that of the above-described position detector 82.

Figure 9:
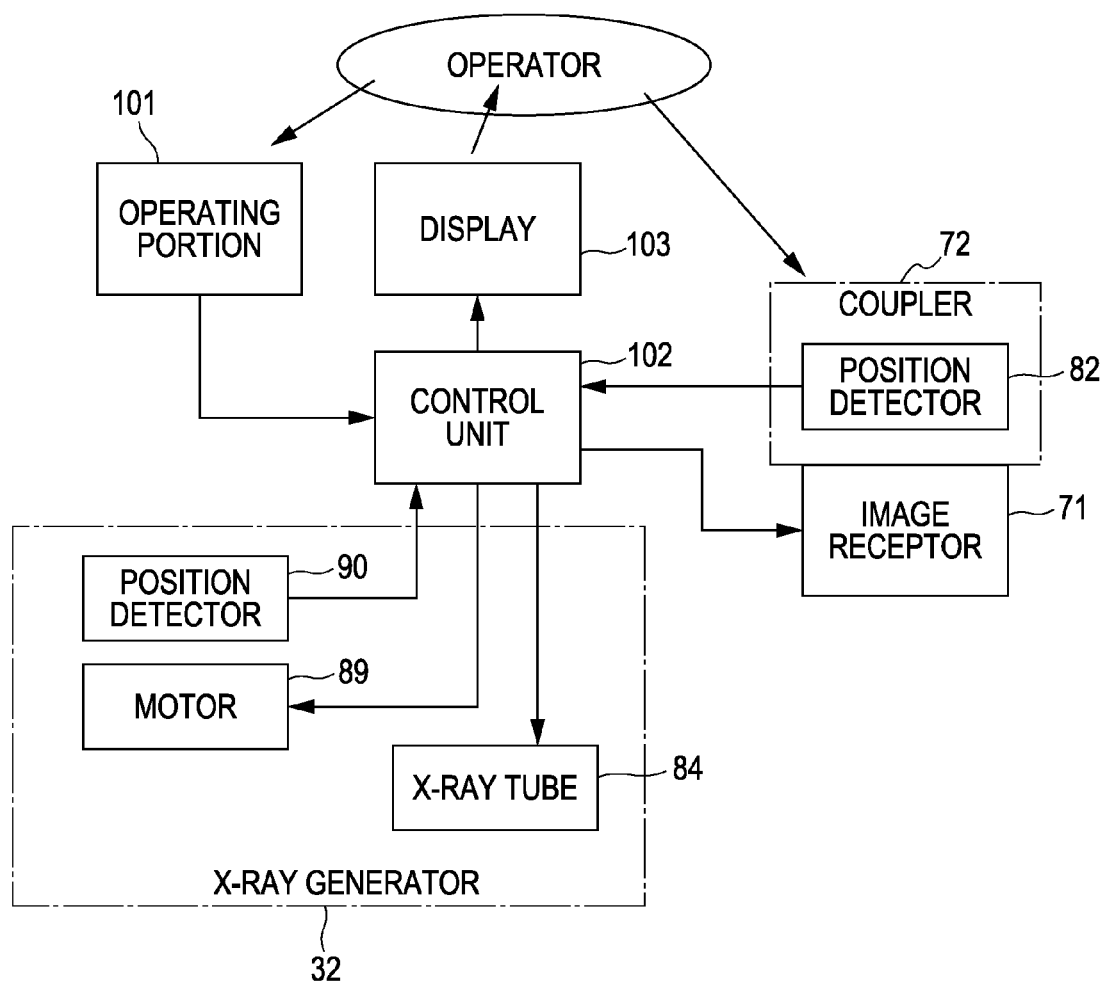
FIG. 9 is a circuit configuration block diagram of an X-ray radiographing apparatus.

FIG. 9 is a circuit configuration block diagram of an X-ray radiographing apparatus. The output of an operating portion 101 is connected to a control unit 102. The output of the control unit 102 is connected to a display 103, an image receptor 71, and an X-ray tube 84 of an X-ray generator 32. The outputs of a position detector 82 of a coupler 72 and a position detector 90 of the X-ray generator 32 are connected to the control unit 102.

Figure 10:
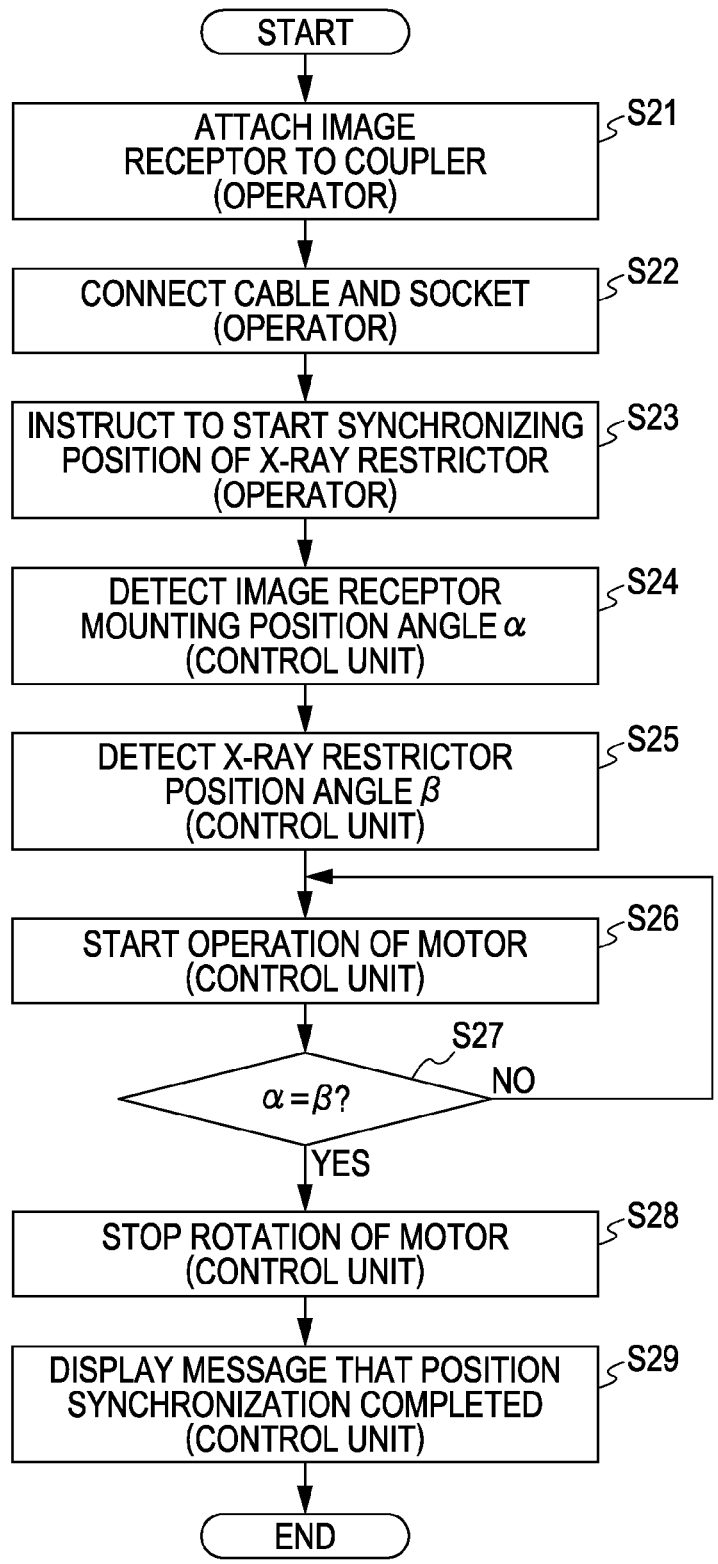
FIG. 10 is a flowchart for synchronizing the position of the X-ray restrictor.
Figure 11:
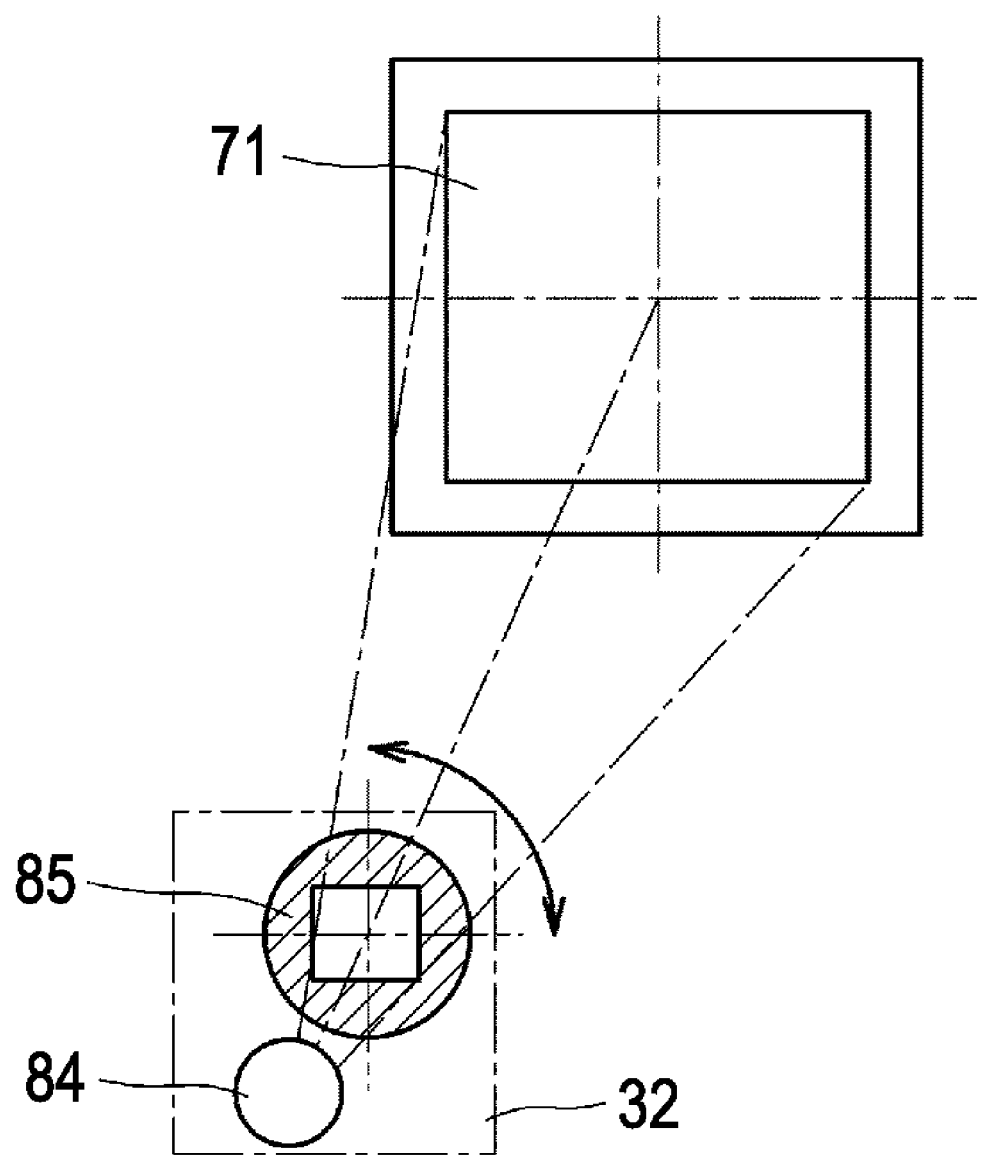
FIG. 11 is a schematic perspective view showing the X-ray restrictor and the image receptor.
Figure 12:
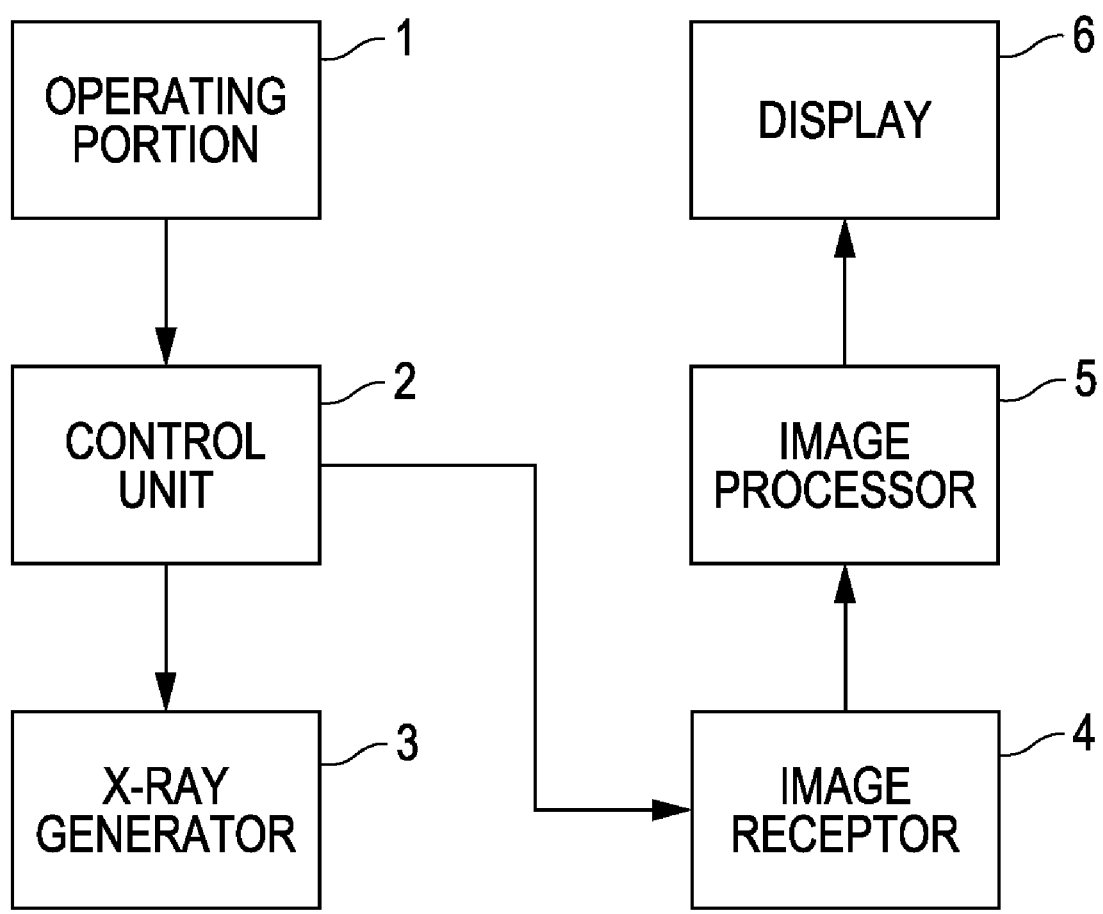
FIG. 12 is a circuit configuration block diagram of a known X-ray radiographing apparatus.
Figure 13:
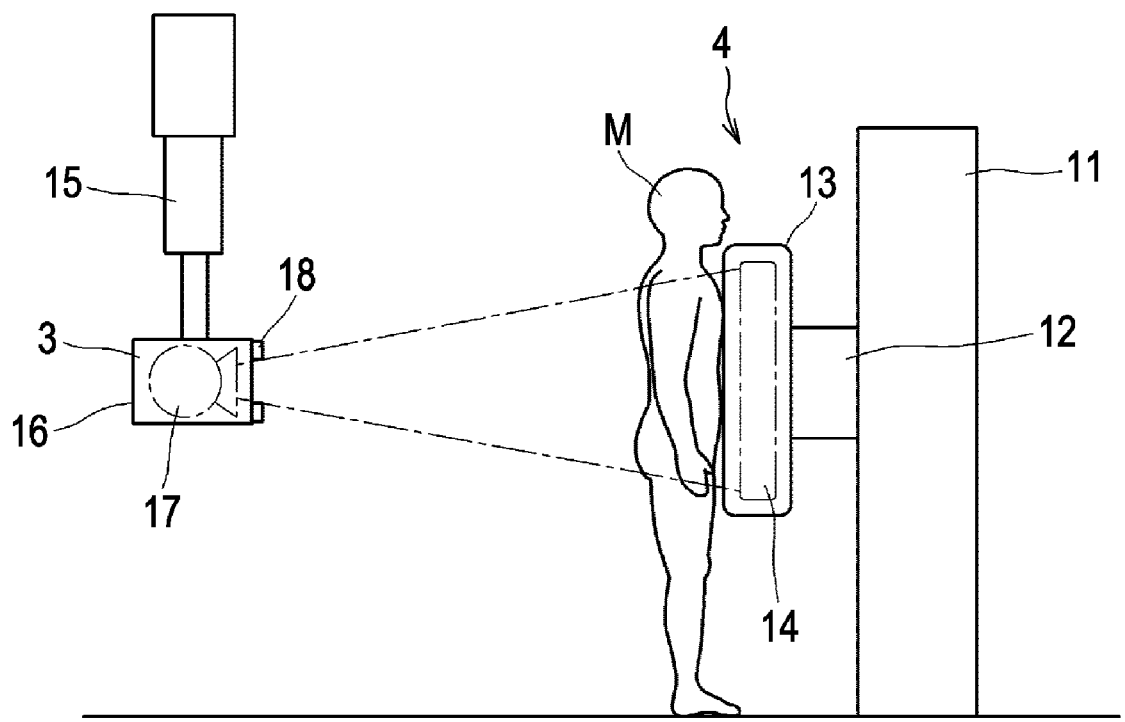
FIG. 13 is an illustration of still image radiographing of the chest and abdomen of a subject in the upright position using a known X-ray radiographing apparatus.
Figure 14:
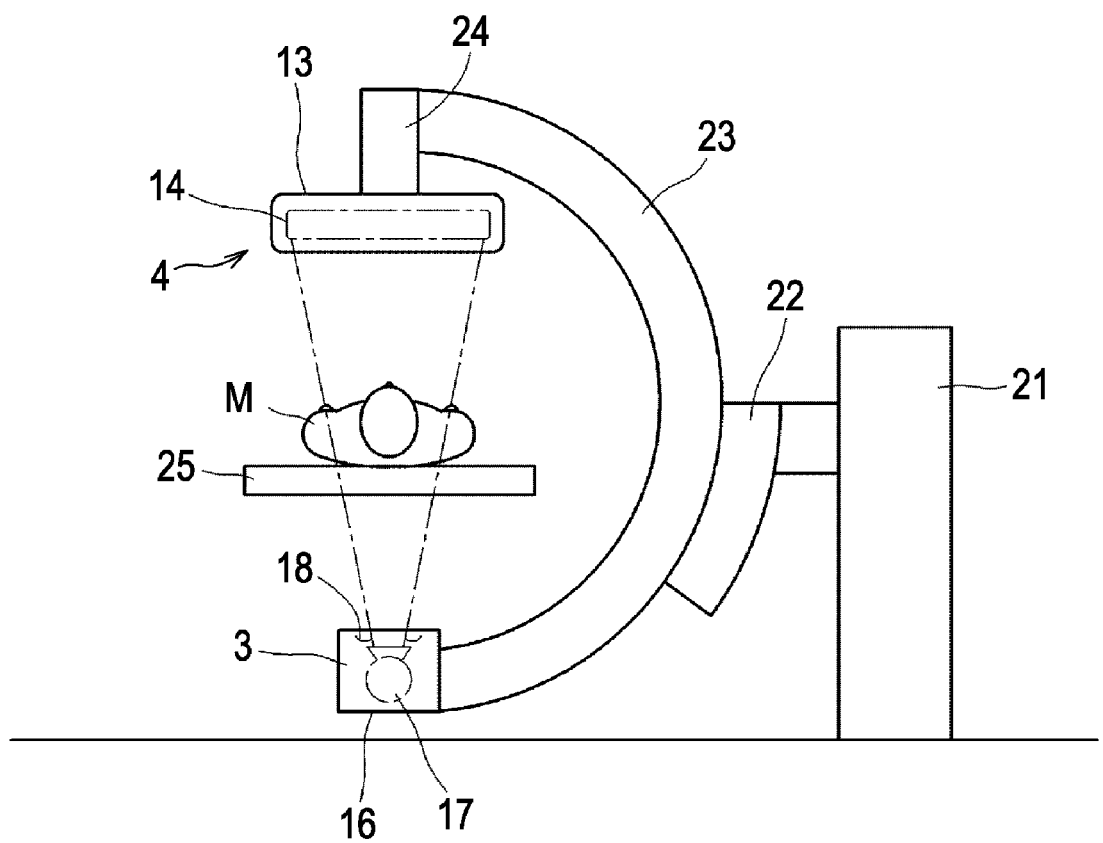
FIG. 14 is an illustration of various types of radiographing of a subject in the recumbent position using a known X-ray radiographing apparatus.

FIG. 10 is a flowchart for synchronizing the position of the X-ray restrictor 85 of the X-ray generator 32. FIG. 11 is a schematic perspective view showing the relationship between the X-ray restrictor 85 and the image receptor 71.

Before the flow of FIG. 10, the image receptor 71 is separated from the coupler 72 of the C-shaped arm 31. When attaching the image receptor 71 to the C-shaped arm 31 to start radiographing, this flow is applied.

The operator attaches the image receptor 71 to the coupler 72 (step S21), connects the cable 39 and the socket 40 (step S22), and then instructs to start synchronizing the position of the X-ray restrictor 85 from the operating portion 101. On the basis of the signal from the position detector 82 of the coupler 72, the position angle of the image receptor 71 relative to the coupler 72 is detected. The obtained value α of angle is a displacement angle from a predetermined initial position (step S24).

Next, on the basis of the signal from the position detector 90 of the X-ray generator 32, the angular position of the X-ray restrictor 85 relative to the case 83 of the X-ray generator 32 is detected. The obtained value β of angle is a displacement angle from a predetermined initial position. When the position angle α of the image receptor 71 is equal to the position angle β of the X-ray restrictor 85, the X-ray irradiation restricted by the X-ray restrictor 85 corresponds to the X-ray irradiation area of the image receptor 71.

In addition to obtaining the position angle α of the image receptor 71 and the position angle β of the X-ray restrictor 85, the control unit 102 starts the operation of the motor 89. The direction of rotation does not make any difference to the effect. However, it is desirable to determine a direction beforehand (step S26).

After starting the operation of the motor 89, the control unit 102 monitors the detection signals of the position detectors 82 and 90. When the position angle α of the image receptor 71 becomes equal to the position angle β of the X-ray restrictor 85, the rotation of the motor 89 is stopped (step S28). At this time, as shown in FIG. 11, X-rays from the X-ray tube 84 are restricted by the X-ray restrictor 85, and the passing X-ray irradiation corresponds to the X-ray detection area of the image receptor 71.

Then, a message that the position synchronization completed is displayed on the display 103 (step S29). So, the operator can learn that the X-ray irradiation restricted by the X-ray restrictor 85 corresponds to the X-ray irradiation area of the image receptor 71. The display 103 is generally a computer display. Instead of or in addition to using a computer display, an electrical bulletin unit or an audio message playback unit can be used.

The operator operates the operating lever 80 and restricts the rotation of the image receptor 71 relative to the coupler 72 to keep the X-ray irradiation area and the X-ray image reception area corresponding to each other. If X-ray irradiation is performed for radiographing in this condition, a favorable image free from underexposed parts can be obtained, and in addition, there is no danger that the surroundings of the area to be exposed are needlessly exposed to X-rays.

Every time the operator changes the position angle of the image receptor 71 relative to the coupler 72, steps S24 to S29 of FIG. 10 may be performed to perform position synchronization. In this case, the X-ray irradiation restricted by the X-ray restrictor 85 corresponds to the X-ray detection area of the image receptor 71 without fail when needed. According to the X-ray radiographing apparatus of the present invention, the image receptor can be attached to the coupler without paying special attention to the position in the angular direction. Therefore, the operation is easy to understand, and the burden on the operator can be reduced.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2008-201431 filed Aug. 5, 2008, which is hereby incorporated by reference herein in its entirety.

What is claimed is:

1. An X-ray radiographing apparatus comprising:
    an X-ray detecting unit having an image reception surface and configured to detect X-rays passing through a subject;
    an image receptor housing the X-ray detecting unit and having a first locking portion;
    a support that supports the image receptor;
    a coupler having a second locking portion and being configured for detachably coupling the image receptor to the support, wherein the first locking portion and the second locking portion are configured to place the image receptor and the coupler in an attached state and a detached state;
    an X-ray generator disposed opposite to the coupler and that emits X-rays towards the image receptor;
    an X-ray restrictor having a rectangular opening and configured to block X-rays from the X-ray generator other than the X-rays passing through the subject;
    a first motor that rotates the X-ray restrictor around an X-ray irradiation axis which is perpendicular to the image reception surface;
    a second motor that rotates the image receptor around the X-ray irradiation axis;
    a detector configured to detect rotation of the image receptor when the second motor rotates the image receptor around the X-ray irradiation axis; and
    a control unit that controls the first motor and the second motor to control a direction of rotation of the X-ray restrictor and a direction of rotation of the image receptor,
    wherein the control unit controls rotation of the second motor and determines an initial position of the image receptor based on an output of the detector when the image receptor is attached to the coupler.

2. The X-ray radiographing apparatus according to claim 1, further comprising a cylindrical surface located between the coupler and the image receptor and centered on the axis perpendicular to the image reception surface, and wherein the image receptor can rotate along the cylindrical surface after the image receptor is attached to the coupler.

3. The X-ray radiographing apparatus according to claim 2, wherein the central axis of the cylindrical surface substantially corresponds to the X-ray irradiation axis.

4. The X-ray radiographing apparatus according to claim 1, wherein, in the attached state, the first locking portion is locked with the second locking portion so as to hold the image receptor and the coupler operatively together.

5. The X-ray radiographing apparatus according to claim 1, wherein the first locking portion includes a movable mechanism, and
    wherein the movable mechanism is operated to place the image receptor and the coupler in the detached state.

6. The X-ray radiographing apparatus according to claim 5, wherein, in the detached state, the image receptor is physically separated from the coupler.

7. The X-ray radiographing apparatus according to claim 5, wherein the movable mechanism includes a mechanical lever.

8. The X-ray radiographing apparatus according to claim 5, wherein the movable mechanism includes a button connected to a spring.

* * * * *